United States Patent [19]

Vaslef et al.

[11] Patent Number: 5,037,383
[45] Date of Patent: Aug. 6, 1991

[54] INTRAVASCULAR LUNG ASSIST DEVICE AND METHOD

[75] Inventors: Steven N. Vaslef, Chicago; Lyle F. Mockros; Robert W. Anderson, both of Glenview, all of Ill.

[73] Assignee: Northwestern University, Evanston, Ill.

[21] Appl. No.: 526,292

[22] Filed: May 21, 1990

[51] Int. Cl.⁵ .............................................. A61M 37/00
[52] U.S. Cl. ........................................ 604/26; 604/49
[58] Field of Search .................... 604/26, 48, 49, 4; 623/1, 9, 12

[56] References Cited

U.S. PATENT DOCUMENTS 3,505,686  4/1970  Bodell ............................ 604/49 X
4,583,969  4/1986  Mortensen ...................... 604/49
4,631,053 12/1986  Taheri ............................. 604/49

Primary Examiner—John D. Yasko
Attorney, Agent, or Firm—Tilton, Fallon, Lungmus

[57] ABSTRACT

An elongated, radially-expandable, intravascular lung assist device is formed by first stretching an elastomeric tubular core, then arranging a plurality of axially-spaced bundles of straight, flexible, hollow fibers formed of gas-permeable material around said core and securing the end portions of each bundle to the core while it is in stretched condition, and then relieving the stretching forces on said core to cause said fibers of each bundle to flex outwardly and form a rosette of outwardly-arched fibers. The core has at least two longitudinal gas-flow passages with lateral openings located at spaced intervals which communicate through manifold chambers at the ends of the bundles for the circulation of gases through the fibers. In use of the device, the core is stretched longitudinally to straighten the bowed fibers and, following insertion of the device into the lumen of a blood vessel, such stretching forces are relieved to allow the bundles to expand radially in situ.

12 Claims, 3 Drawing Sheets

INTRAVASCULAR LUNG ASSIST DEVICE AND METHOD

BACKGROUND AND SUMMARY

There has been a continuing need for a simple, effective, and relatively inexpensive lung assist device for supplying oxygen and removing carbon dioxide from patients suffering from acute illnesses such as pneumonitis, atelectasis, various heart and circulatory ailments, fluid in the lungs, obstruction of pulmonary ventilation, or lung injury caused by heat, noxious gases, or other factors. Prior techniques for so assisting the lungs fall into three general categories: respirators, extracorporeal oxygenators, and intravascular lung assist devices.

Respirators improve the efficiency of a patient's lungs but are less than suitable for use in those situations where a patient's damaged or diseased lungs require rest or are simply incapable of performing the work needed for adequate respiration. Extracorporeal oxygenators usually take the form of membrane oxygenators (ECMOs) commonly referred to as heart-lung machines and are most frequently used for relatively snort intervals, as during surgery where the circulation through a patient's heart and lungs is temporarily bypassed. Reports of successful longer-term usage of ECMOs in adults, except for particular categories of patients suffering from specific types of circulatory problems, have generally been lacking. Further, it is apparent that the use of ECMOs not only involves the deployment of expensive equipment but requires constant supervision and control by teams of skilled technicians. ECMO usage also necessitates the use of anticoagulants which may present problems of internal bleeding, especially when administered on a longer-term basis.

Intravascular lung assist devices (ILADs) are believed to overcome many of the shortcomings of respirators and extracorporeal oxygenators. U.S. Pat. No. 4,583,969 discloses a mass transfer device intended to be inserted into a patient's vena cava to provide extrapulmonary in vivo oxygenation of the blood. The device takes the form of a bundle of tiny gas-permeable tubes that extend between a pair of headers connected to gas (oxygen) supply means and to gas exhaust means, respectively. When located in the vena cava, the device operates as an intravascular artificial lung to assist the operation of a patient's diseased or damaged lungs. Reference may also be had to related U.S. Pat. Nos. 4,631,053 and 3,505,686 as further illustrating the state of the art.

Despite their advantages, prior ILADs have disadvantages that largely offset their usefulness. A chief shortcoming is their relatively poor gas-transfer efficiency. Another is size; if such a device is small enough to be inserted into the body through the femoral, iliac, or jugular veins, it does not efficiently utilize, for purposes of gas transfer, the lumen space at the ultimate location in the vena cava, and if the device were sized for more efficient performance at its operative site, it would be too large for introduction into the body through the branch veins.

Accordingly, a main aspect of this invention lies in providing an ILAD that overcomes or greatly reduces the problems associated with prior intravascular lung assist devices. In particular, this invention is concerned with an ILAD that is radially expandable in situ to provide relatively high gas transfer efficiency in use. Such efficiency is achieved not only because of the relatively large surface area exposed to blood flow, but also because of the cross flow arrangement of fibers that minimizes blood channeling around the device and the relatively short gas pathways and parallel flow circuitry involved.

In brief, the device takes the form of an elastomeric tubular core with longitudinal gas inflow and outflow passages. A plurality of bundles of flexible but relatively non-stretchable hollow fibers formed of gas-permeable polymeric material surround the elastomeric core, each of the bundles having end portions spaced from those of adjacent bundles and being fixed to the core by mounting collars and suitable embedding or potting means. Each of the bundles also has a flexible intermediate portion in which the fibers are substantially straight and parallel when the core is in stretched condition but in which the fibers flex outwardly to form a rosette of outwardly-bowed fibers when the axial stretching forces on the core are relieved. The core has lateral apertures disposed within the mounting collars for placing the end portions of successive hollow fiber bundles in flow communication with such passages. Such apertures are arranged to communicate alternately with the inflow and outflow passages within successive mounting collars along the length of the core. The bundles are therefore paired and arranged as subunits with parallel (rather than serial) flow of gases to and from the bundles of successive subunits.

The method of forming the ILAD of this invention involves the steps of first longitudinally stretching the elastomeric tubular core, then arranging a plurality of longitudinally-spaced bundles of hollow, flexible, gas-permeable fibers around the core, securing the end portions of each bundle to the core while the core is in its longitudinally stretched condition and the fibers are substantially straight, providing lateral openings in the core communicating with longitudinal inflow and outflow passages extending through the core, such openings alternately communicating with such inflow and outflow passages in the spaces between the end portions of successive bundles of fibers, and finally enclosing the spaces between successive bundles by collar elements that provide manifold chambers for the inflow and outflow of gases into and from the hollow fiber bundles. Thereafter, when the longitudinal stretching forces on the core are relieved, the core contracts axially and the fibers of each bundle flex outwardly to form a rosette of outwardly-bowed hollow fibers.

Since each manifold chamber between a pair of adjacent fiber bundles serves either as an inlet chamber or an outlet chamber, depending on the core passage with which it communicates, and since there is an alternating arrangement of inlet and outlet chambers along the bundle-providing length of the device, it is believed apparent that each manifold chamber serves two such bundles (except at the extreme ends of the series), that each pair of bundles constitutes an operating subunit, and that the gases flowing through the pair of bundles of each such subunit travel in opposite axial directions.

In a second embodiment of the invention, each bundle has one or more restraining rings extending about its intermediate portion. In such a construction, when the stretching forces on the elastomeric core are relieved, a rosette of outwardly-bowed fibers is formed on opposite sides of each such restraining ring.

In the use of the device, the elastomeric core is first stretched axially to cause the fibers of the bundles to straighten. Such longitudinal stretching may be achieved by any suitable means such as by inserting a relatively rigid member into at least one of the flow passages of the core. The device in its radially contracted condition is then inserted into the lumen of a blood vessel such as the femoral vein or artery. When the bundle-providing portion of the device has been advanced to its operative site in the vena cava or aorta, the core is permitted to retract longitudinally (as by withdrawing the rigid member from the core), thereby causing the fibers of the bundles to expand outwardly into a series of rosettes of outwardly-bowed fibers.

Other features, advantages, and objects of the invention will become apparent from the specification and drawings.

DRAWINGS

Figure 6:
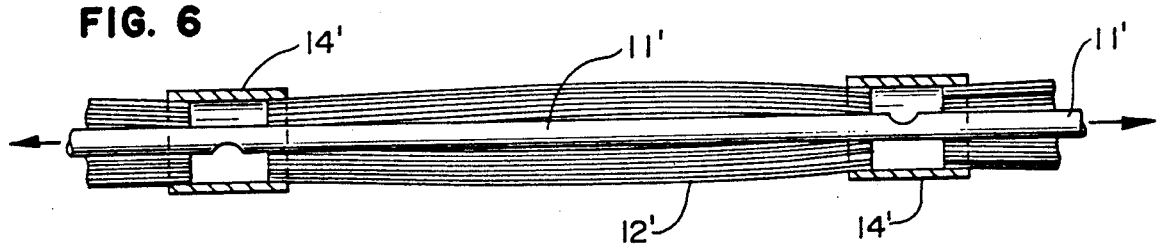
Figure 7:
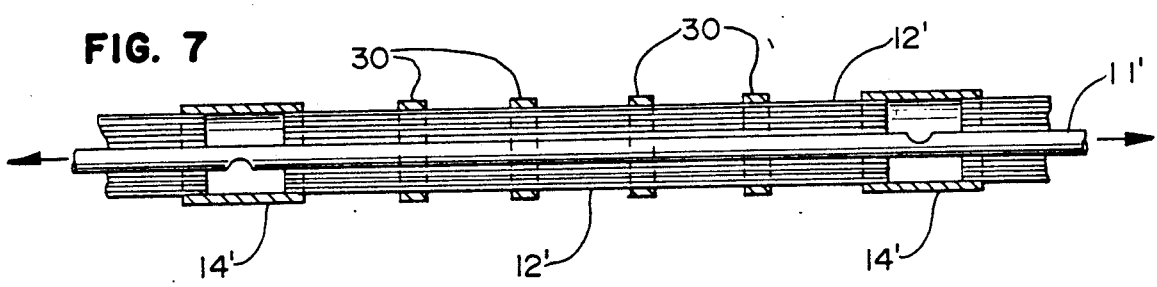
Figure 8:
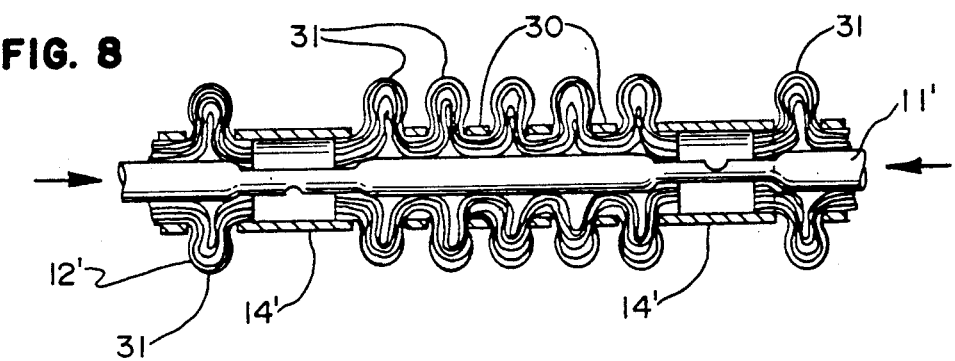

FIGS. 6, 7, and 8 are longitudinal sectional views depicting successive steps in making a lung assist device constituting a second embodiment of the invention.

DETAILED DESCRIPTION OF PREFERRED EMBODIMENTS

Figure 1:
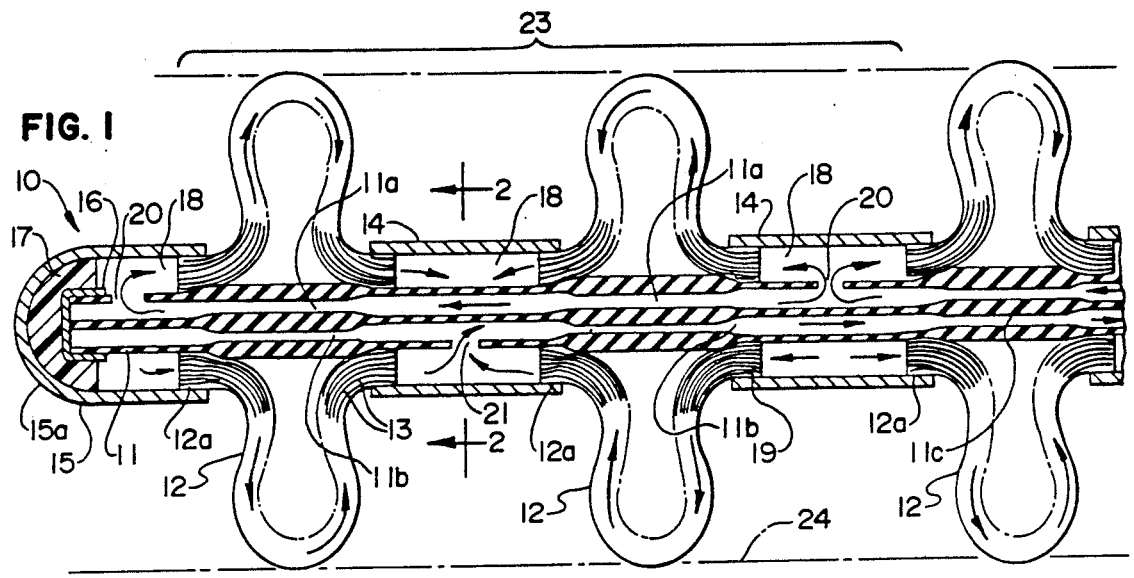
FIG. 1 is a somewhat schematic longitudinal cross sectional view of a portion of an intravascular lung assist device embodying this invention while in place in the vena cava or aorta.
Figure 2:
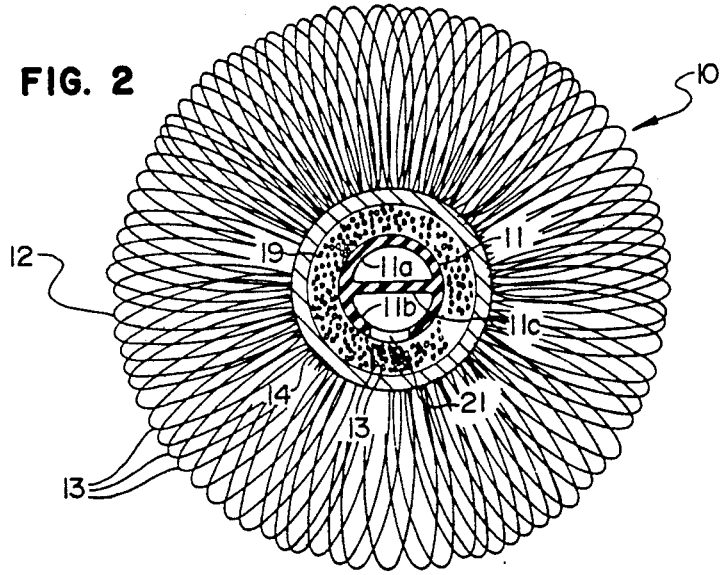
FIG. 2 is a sectional view taken along line 2—2 of FIG. 1.
Figure 3:
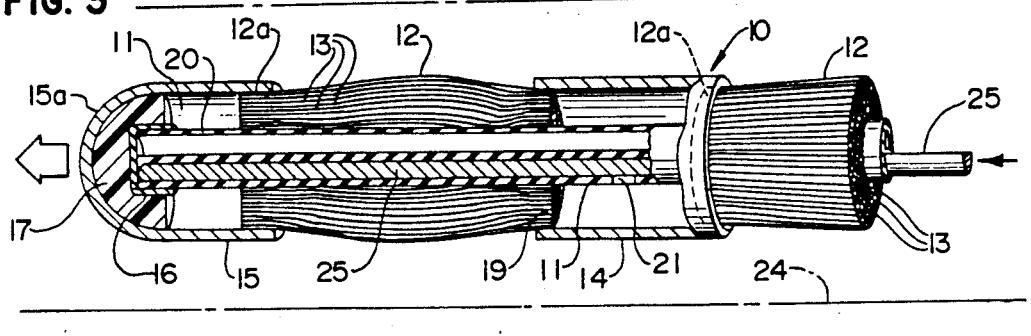
FIG. 3 is a longitudinal perspective view, shown partly in section, illustrating the relationship of parts when a relatively rigid insert member is utilized to stretch the elastomeric core and thereby straighten the bundles of fibers.

Referring to FIGS. 1-3 of the drawings, the numeral 10 generally designates an intravascular lung assist device (ILAD) having an elastomeric tubular core 11 and a plurality of bundles 12 of flexible hollow fibers surrounding the core with the end portions 12a of successive bundles being spaced apart and held in place by mounting collars 14. At the distal end of the device, a modified mounting collar 15 is provided with a smoothly rounded end or tip 15a. Closure means in the form of a cap 16 seals off the end of tubular core 11 within distal mounting collar 15. A potting compound 17 of epoxy or any other suitable material secures cap 16 in place within collar 15.

As shown most clearly in FIG. 2, the elastomeric core 11 has at least two lumens 11a and 11b separated by a longitudinal septum 11c. One of the lumens 11a is for gas (oxygen) inflow, the other 11b for gas outflow. The core may be formed of any highly stretchable and elastically-recoverable material. Silicone rubber has been found suitable, but other materials having similar properties may be used. While the core preferably takes the form of a single tube with a pair of lumens divided by a longitudinal septum, it will be understood that the core may instead comprise two (or more) parallel tubes that may be either separate from or attached to each other.

Unlike the material of the core, the material from which the flexible fibers of each bundle is formed is relatively non-stretchable. It is also essential that the fibers 13 be hollow, flexible, and gas-permeable. While tubes of various polymeric compositions having such properties are well known, microporous polypropylene fibers having an outside diameter of 290 microns have been found particularly effective for this application.

It will be noted from FIGS. 1 and 3 that the ends 12a of adjacent bundles 12 are spaced apart within mounting collars 14. Each collar defines a manifold chamber 18 that communicates with the open ends of the tiny fibers secured by the collar. To prevent leakage and to hold the ends of the fibers in place, embedding or potting means 19 externally binds the end portions 12a of the fibers within opposite ends of each mounting collar 14. A polyurethane compound has been effectively used as the potting agent but any other suitable material capable of externally bonding the ends of the fibers together, and to the interior of a mounting collar 14 at each end thereof, may be used.

An aperture is formed in the wall of the tubular core within each manifold chamber 18 for the flow of gases into or out of the chamber. In the illustration given, a core aperture 20 in every other manifold chamber of the series serves as an oxygen supply port for the two bundles 12 immediately adjacent to and communicating with each such supply manifold. It is to be noted that the sizes of the apertures in the core may be varied with axial position so as to evenly distribute gases to successive bundles. Thus, supply ports 20 may be of progressively increasing size in a distal direction to insure a more uniform distribution of gases to such bundles.

The alternate manifolds—those disposed between the supply manifolds of the series—constitute gas return manifolds. In each such return manifold, the wall of core 11 is provided with a side aperture 21 which serve as a gas return port (FIGS. 1, 2). Therefore, the supply and return ports each communicate with a pair of adjacent bundles 12 except where such a supply or return port happens to be at the extreme end of the series of bundles. An operative subunit therefore consists of two bundles and two mounting collars surrounding an elastomeric tubular core which is ported to provide a supply manifold in one of the collars and a return manifold in the other. Such a subunit is indicated by numeral 23 in FIG. 1.

FIG. 1 illustrates the device in a radially-expanded condition as it might appear within the lumen 24 of a major vessel such as the vena cava or aorta. The flexible fibers of each bundle are severely arched or bowed in a longitudinal direction and, when such a bundle is viewed from the end, the multiplicity of arched fibers present a rosette appearance (FIG. 2). Ideally, the arched fibers closely approach and may even contact the lining of the vessel with the result that the blood traveling through the lumen of the vessel cannot readily bypass the device. As the blood contacts the radially-extending or cross-flow fibers, some mixing occurs which enhances mass transfer efficiency. It has been found that the efficiency of oxygen transfer (flux) increases with the degree to which the fibers 13 are arranged in a cross-flow configuration, with such flux also increasing with increases of hemoglobin desaturation and blood flow rate. Carbon dioxide flux similarly depends upon the extent to which the fibers are arranged in a cross-flow pattern and upon blood flow rate, as well as on gas flow rate and gas path length.

It is to be emphasized that the gas path length through each bundle is relatively short and that the subunits are arranged so that they operate in parallel rather than in series. Because of the shortness of the gas pathways through the hollow fibers, the gas pressure drop through the system may be kept relatively low. That in turn reduces the need for drawing a large vacuum at the proximal end of outflow passage 11b to maintain effective gas flow through the system. Also, by keeping the pathways short, the partial pressure of carbon dioxide in the fiber bundles, regardless of the location of such bundles along the length of the device, may be maintained at a low enough level to promote more effective removal of carbon dioxide from the blood than in systems having longer gas pathways.

The device may be introduced into a major vessel such as the vena cava or aorta through a branch vessel such as the femoral or iliac vessels. For that purpose, the diameter of the device is reduced by longitudinally stretching the tubular core 11 and thereby straightening the fibers of bundles 12 (FIG. 3). Such stretching action may be achieved by inserting a relatively stiff rod-like member 25 into one or both passages 11a, 11b of the core to cause those portions of the core surrounded by the bundles of hollow fibers to stretch to substantially the full length of the straightened fibers. Suitable means (not shown) are provided at the proximal end (not shown) of the device for temporarily immobilizing the insert member 25 within the stretched core. While the use of a relatively stiff insert member is believed to be a preferred technique for stretching the core and temporarily straightening the fibers, it is to be understood that other means, including means external to the device, might be used to achieve similar results.

When the device has been advanced through the branch vessel into its operative site in the vena cava or aorta, the insert member 25 is withdrawn and the elastic core returns to the condition shown in FIG. 1 in which the fibers of each of the bundles flex radially outwardly to form a rosette of outwardly-arched fibers. Oxygen is then supplied through inflow passage 11a with mass transfer occurring through the walls of the fibers serving as tubular diffusion membranes. The intravascular artificial lung thereby assists if not supplants the action of a patient's natural lung during treatment and/or recuperation.

Removal of the device is achieved by reversing the steps of its introduction. The device is first axially extended to cause radial contraction of the fiber bundles and is then withdrawn from the vascular system.

Figure 4:
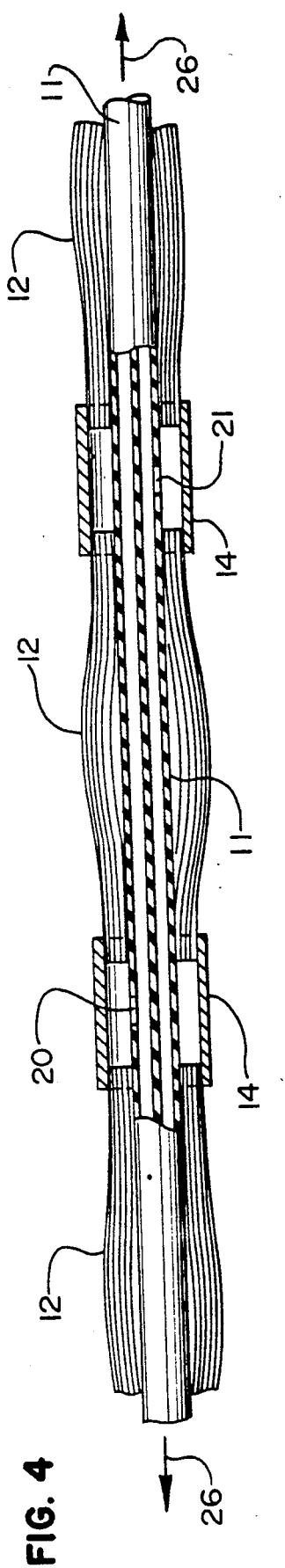
FIG. 4 is a longitudinal sectional view illustrating a step in the manufacture of the device in which the fiber bundles are arranged and end potted while the elastomeric core is in stretched condition.
Figure 5:
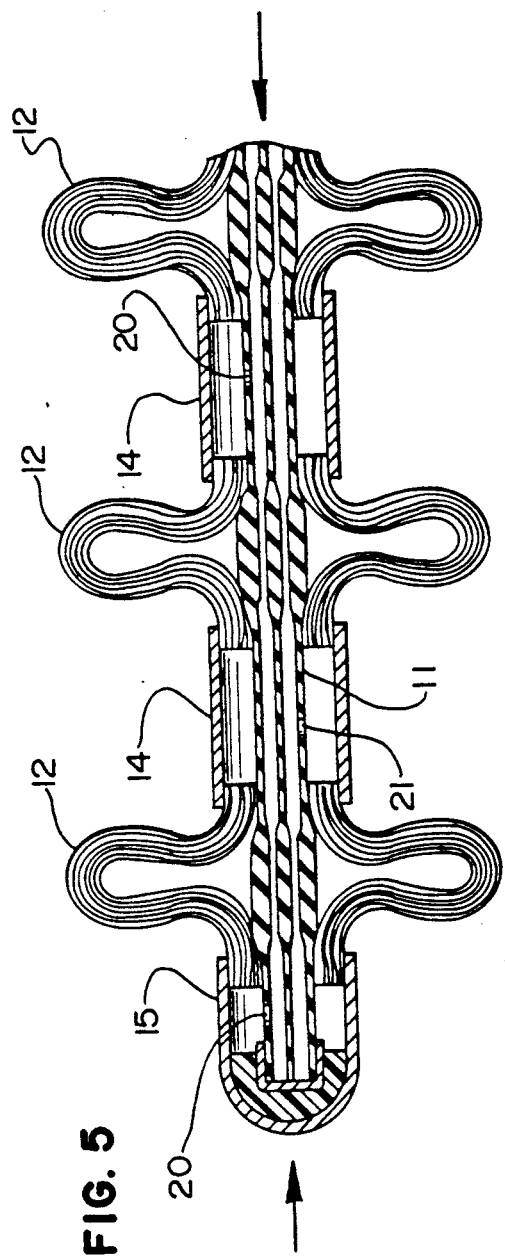
FIG. 5 is a longitudinal sectional view illustrating a subsequent manufacturing step in which the longitudinal stretching forces on the core are relieved.

FIGS. 4 and 5 illustrate two steps in the method of forming an intravascular lung assist device embodying this invention. In FIG. 4, core 11 is shown in stretched condition with the stretch forces being indicated by arrows 26. While the core is so stretched, the fiber bundles 12 are arranged about and along the core with the fibers of such bundles being straight and generally parallel with the stretched core. The ends of the fibers are potted and secured within mounting collars 14. Thereafter, the stretching forces are removed and those portions of the core surrounded by the fibers are allowed to retract, causing the fibers to flex radially outwardly to form the rosettes of outwardly-arched fibers as already described (FIG. 5).

FIGS. 6-8 depict a second embodiment of the invention and the method of forming it. FIG. 6 shows a method step similar to that of FIG. 4 with core 11' in stretched condition and the fibers of surrounding bundle 12' relatively straight with their end portions secured and potted within mounting collars 14'. Before relieving the stretching forces applied to core 11', one or more restraining rings 30 are fitted about the intermediate portion of bundle 12' between each pair of collars 14'. In FIG. 7, four such restraining rings are shown but a greater or smaller number may be provided as desired. When the stretching forces are removed and the core 11' is allowed to retract, a rosette 31 of outwardly-bowed fibers is formed on opposite sides of each restraining ring 30. Where four restraining rings are used, a total of five rosettes 31 are therefore formed by each bundle 12' of hollow fibers.

Except for the provision of one or more restraining rings 30 that control the outward bowing action of each fiber bundle 12' when the stretching forces applied to core 11 are removed, the embodiment of FIG. 8 is substantially the same as that of FIGS. 1-3. The utilization of restraining rings 30 permits an increase in density of cross-flow fibers for any given length of device. Because the axial dimension of a restraining ring 30 may be substantially less than that of a mounting collar 14' (see FIG. 7), the same result—increased density of cross-flow fibers exposed to blood flow—cannot be achieved as effectively in the first embodiment simply by increasing the number of mounting collars 14 or decreasing the spacing between them.

An ILAD designed for placement in the vena cava or aorta should have an operating length of 30 to 40 centimeters and an insertion outside diameter of not more than 1.5 centimeters, preferably 1.0 centimeters or less. When stretching forces are removed and the elastic core retracts, the rosettes of outwardly-bowed fibers should increase the diameter of the device from 1.5 to 4 times depending on the construction employed and, in the case of the second embodiment, the number of restraining rings utilized.

While in the foregoing we have disclosed an embodiment of the invention in considerable detail for purposes of illustration, it will be understood by those skilled in the art that many of these details may be varied without departing from the spirit and scope of the invention.

What is claimed is:

1. An intravascular lung assist device comprising an elastomeric tubular core having longitudinal gas inflow and outflow passages therein; a plurality of bundles of flexible hollow fibers formed of gas-permeable polymeric material surrounding said elastomeric core; said bundles each having end portions spaced from the end portions of adjacent bundles and fixed to said core by a plurality of spaced mounting collars having embedding means disposed within said collars but external to said end portions of said hollow fibers; said bundles also each having a flexible intermediate portion in which the fibers thereof are substantially straight and parallel when said core is stretched axially and in which said fibers flex outwardly to form a rosette of outwardly-arched fibers when axial stretching forces on said core are removed; said core having lateral apertures disposed within said mounting collars for placing the end portions of successive hollow fiber bundles in flow communication with said passages.

2. The device of claim 1 in which said lateral apertures of said core are arranged to alternately communicate with said inflow and outflow passages within successive mounting collars along the length of said core, whereby the gas flow through successive bundles is in alternately reversing directions.

3. The device of claim 2 in which said lateral apertures are of varying size along said core to provide even distribution of gases to successive fiber bundles.

4. The device of claim 1 in which said hollow fibers of said bundles are substantially non-stretchable.

5. The device of claim 1 in which each of said bundles has at least one restraining ring extending about said intermediate portion thereof, whereby, a rosette of outwardly-arched fibers is formed on opposite sides of each restraining ring when axial stretching forces on said core are removed.

6. A method of forming an intravascular lung assist device comprising the steps of longitudinally stretching an elastomeric tubular core having first and second flow passages extending longitudinally therethrough; arranging a plurality of longitudinally-spaced bundles of hollow, flexible, gas-permeable fibers around said core; securing end portions of each of said longitudinally-spaced bundles to said core while said core is longitudinally stretched and said fibers are substantially straight and parallel with said core; providing lateral apertures in said core communicating with said first and second passages in the spaces between the end portions of successive bundles and enclosing said spaces by mounting collars to provide manifold chambers for the inflow and outflow of gases into and from said hollow fiber bundles; whereby, when the longitudinal stretching forces on said core are relieved, said core contracts axially and the fibers of each bundle flex outwardly to form a rosette of outwardly-arched hollow fibers.

7. The method of claim 6 in which said step of providing lateral apertures in said core includes arranging said apertures so that they communicate alternately with said first and second flow passages in successive manifold chambers along the length of said device.

8. The method of claims 6 or 7 in which there is the further step of relieving the longitudinal stretching forces on said core to allow said core to contract axially and said bundles of fibers to flex radially outwardly to form rosettes of outwardly-arched hollow fibers.

9. The method of claim 8 in which there are the further steps of subsequently stretching said core to straighten the fibers of each bundle and then inserting said device into the lumen of a vessel while said core is stretched and said fibers are straightened; and thereafter permitting said core to retract longitudinally and said bundles to expand radially outwardly into rosettes of outwardly-arched fibers within said lumen.

10. The method of claim 9 in which said step of subsequently stretching said core is performed by inserting a relatively rigid member into at least one of said flow passages, said core thereafter being permitted to retract longitudinally by removing said relatively rigid member from said flow passage.

11. The method of claim 9 in which there is the further step of removing said device from the lumen of a vessel by again stretching said core to radially contract said bundles and then axially withdrawing said device from said vessel.

12. The method of claim 6 in which at least one restraining ring is placed around each bundle intermediate the end portions thereof while said core is in stretched condition; said ring having an axial dimension substantially less than the length of each bundle between the mounting collars thereof.

* * * * *